United States Patent
Herken (10) Patent No.: US 9,427,597 B2
(45) Date of Patent: Aug. 30, 2016

(54) DETECTION OF REDUCED DEFIBRILLATION PAD CONTACT

(71) Applicant: ZOLL MEDICAL CORPORATION, Chelmsford, MA (US)

(72) Inventor: Ulrich Herken, Medford, MA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 0 days.

(21) Appl. No.: 14/199,344

(22) Filed: Mar. 6, 2014

(65) Prior Publication Data

US 2014/0257422 A1 Sep. 11, 2014

Related U.S. Application Data (60) Provisional application No. 61/774,082, filed on Mar. 7, 2013.

(51) Int. Cl.
*A61N 1/39* (2006.01)
*A61N 1/04* (2006.01)

(52) U.S. Cl.
CPC .............. *A61N 1/3925* (2013.01); *A61N 1/046* (2013.01); *A61N 1/3993* (2013.01); *A61N 1/3931* (2013.01)

(58) Field of Classification Search
None
See application file for complete search history.

(56) References Cited

U.S. PATENT DOCUMENTS

| | | | | |
|---|---|---|---|---|
| 4,610,254 A | * | 9/1986 | Morgan et al. | 607/6 |
| 5,247,939 A | * | 9/1993 | Sjoquist et al. | 600/510 |
| 8,060,199 B2 | * | 11/2011 | Walker et al. | 607/5 |
| 8,369,944 B2 | | 2/2013 | Macho et al. | |
| 2004/0116969 A1 | * | 6/2004 | Owen et al. | 607/6 |
| 2004/0267325 A1 | | 12/2004 | Geheb et al. | |
| 2008/0103535 A1 | | 5/2008 | Ostroff et al. | |
| 2008/0188721 A1 | * | 8/2008 | Patangay et al. | 600/301 |
| 2009/0171344 A1 | * | 7/2009 | Pontis | 606/35 |
| 2012/0232355 A1 | | 9/2012 | Freeman | |
| 2012/0245648 A1 | | 9/2012 | Elghazzawi et al. | |

OTHER PUBLICATIONS

International Search Report from corresponding PCT application No. PCT/US2014/021228.

* cited by examiner

*Primary Examiner* — Erica Lee
(74) *Attorney, Agent, or Firm* — The Webb Law Firm (57) ABSTRACT

A system and method of detecting a loss of electrical contact between a pair of electrodes that are electrically coupled to skin of a subject. The method includes monitoring parameters of a transthoracic impedance between the pair of electrodes in at least one of a low frequency regime and a high frequency regime, detecting an occurrence of chest compressions based on a signal indicative of chest compressions, establishing baseline levels of the parameters in at least one of the low and high frequency regimes, detecting whether changes in at least one parameter exceeds the baseline level by a threshold, determining that at least one electrode of the pair of electrodes is losing electrical contact with the skin responsive to the at least one parameter exceeding the baseline level by the threshold, and issuing an alert in response to a determination that the at least one electrode is losing electrical contact.

18 Claims, 10 Drawing Sheets

DETECTION OF REDUCED DEFIBRILLATION PAD CONTACT

CROSS REFERENCE TO RELATED APPLICATIONS

This application claims priority under 35 U.S.C. §119(e) to U.S. Provisional Application Ser. No. 61/774,082 titled "DETECTION OF REDUCED DEFIBRILLATION PAD CONTACT," filed Mar. 7, 2013, which is incorporated herein by reference in its entirety.

BACKGROUND

1. Field of the Invention

The present invention is directed to medical electrodes and electrode systems, and more particularly, to medical electrodes that may be used with a medical device, such as a defibrillator.

2. Discussion of Related Art

Cardiac arrest and other cardiac health ailments are a major cause of death worldwide. Various resuscitation efforts aim to maintain the body's circulatory and respiratory systems during cardiac arrest in an attempt to save the life of the victim. The sooner these resuscitation efforts begin, the better the victim's chances of survival.

To aid victims experiencing cardiac arrest, many emergency responders (such as EMTs, Policemen and Policewomen, Firemen and Firewomen, etc.) are trained in the operation of automated external defibrillator (AED) devices, and carry such devices with them in their response vehicle. AED devices are often also deployed in common carriers such as an airplane, a train, or a bus, in hotels or businesses, and elsewhere. An AED is a portable electronic device that is able to treat a subject experiencing life-threatening cardiac arrhythmia through defibrillation. The electrical energy supplied by defibrillation ideally stops the arrhythmia, allowing the heart of the subject to reestablish an effective rhythm. Some AEDs have the capability of automatically diagnosing the potentially life threatening cardiac arrhythmias of ventricular fibrillation and ventricular tachycardia in a subject, and some AEDs are designed to be simple enough in operation to be utilized by a layman and provide simple audio and visual commands to direct their use. Examples of AED devices include Advanced Life Support (ALS) AED devices, such as the E Series, M Series, R Series, or X Series defibrillators, as well as Basic Life Support (BLS) AED devices, such as the AED Pro or AED Plus defibrillator, each available from ZOLL Medical Corporation of Chelmsford Mass.

SUMMARY

In accordance with one aspect of the present invention, a life support device is provided. The life support device comprises a pair of electrodes configured to be attached to a skin of a subject, a therapy interface electrically coupled to the pair of electrodes, and a transthoracic impedance monitor electrically coupled to the therapy interface. The transthoracic impedance monitor is configured to monitor transthoracic impedance parameters of a transthoracic impedance between the pair of electrodes in at least one a low frequency regime below a set frequency and a high frequency regime at or above the set frequency, to detect CPR chest compressions based on a signal indicative of the CPR chest compressions, to establish baseline levels of the transthoracic impedance parameters corresponding to the at least one of the low frequency regime and the high frequency regime, to detect whether changes in at least one transthoracic impedance parameter exceeds the baseline level by a threshold, to determine that at least one electrode of the pair of electrodes is losing electrical contact with the skin of the subject in response to detecting that the changes in the at least one transthoracic impedance parameter exceeds the baseline level by the threshold, and to issue an alert in response to a determination that the at least one electrode of the pair of electrodes losing electrical contact with the skin of the subject.

In accordance with another aspect of the present invention, a method of detecting a loss of electrical contact between a pair of electrodes that are electrically coupled to a skin of a subject is provided. The method comprises acts of monitoring transthoracic impedance parameters of a transthoracic impedance between the pair of electrodes in at least one of a low frequency regime below a set frequency and a high frequency regime at or above the set frequency, detecting an occurrence of CPR chest compressions based upon a signal indicative of the CPR chest compressions, establishing baseline levels of the transthoracic impedance parameters in at least one of the low frequency regime and the high frequency regime, detecting whether changes in at least one transthoracic impedance parameter exceeds the baseline level by a threshold, determining that at least one electrode of the pair of electrodes is losing electrical contact with the skin of the subject in response to the at least one transthoracic impedance parameter exceeding the baseline level by the threshold, and issuing an alert in response to a determination that the at least one electrode of the pair of electrodes is losing electrical contact with the skin of the subject. In accordance with a further aspect of the present invention, a computer readable medium is provided that is encoded with a set of instructions, that, when executed by a processor of a life support device, performs the above-described method.

In accordance with yet a further aspect of the present invention, a life support device is provided comprising a pair of electrodes configured to be attached to a skin of a subject, a therapy interface electrically coupled to the pair of electrodes, and a transthoracic impedance monitor electrically coupled to the therapy interface. In accordance with one embodiment, the transthoracic impedance monitor is configured to monitor transthoracic impedance parameters of a transthoracic impedance between the pair of electrodes in at least one a low frequency regime below a set frequency and a high frequency regime at or above the set frequency, to establish baseline levels of the transthoracic impedance parameters corresponding to the at least one of the low frequency regime and the high frequency regime, to detect whether changes in at least one transthoracic impedance parameter exceeds the baseline level by a threshold, to determine that at least one electrode of the pair of electrodes is losing electrical contact with the skin of the subject in response to detecting that the changes in the at least one transthoracic impedance parameter exceeds the baseline level by the threshold, and to issue an alert in response to a determination that the at least one electrode of the pair of electrodes losing electrical contact with the skin of the subject.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof as well as additional items.

Figure 1:
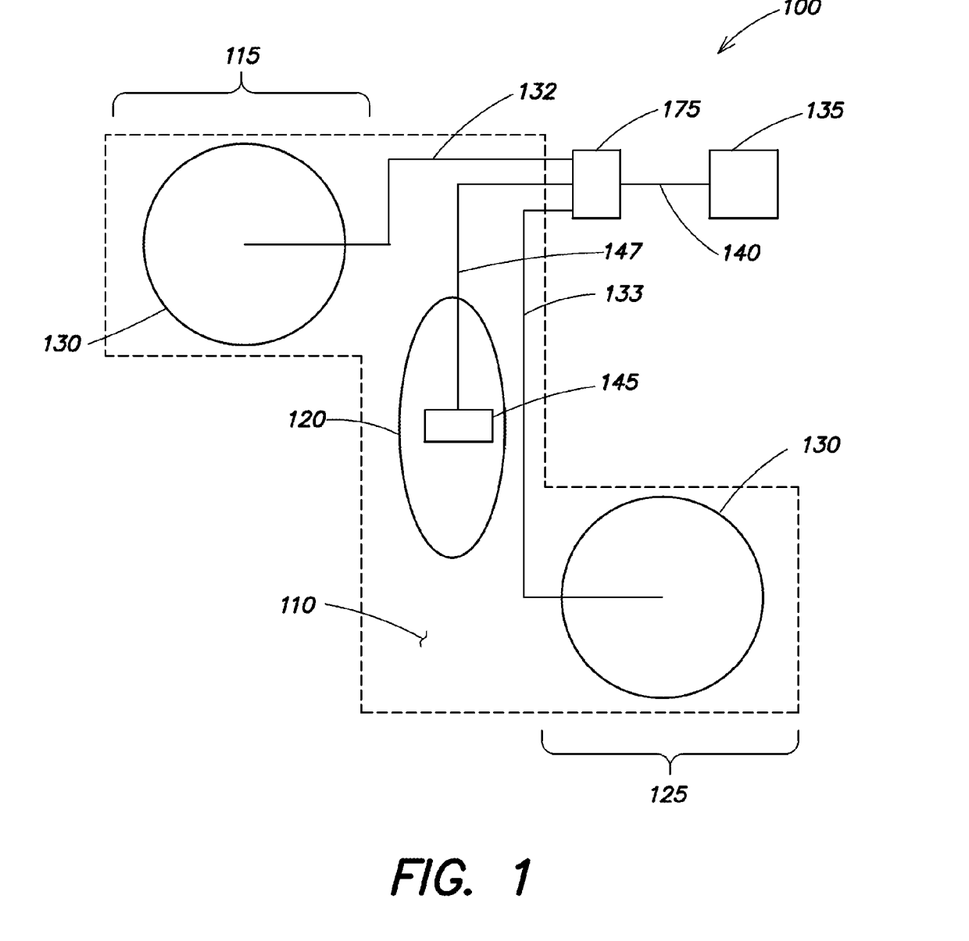
FIG. 1 is a schematic illustration of an electrode system that may be used in accordance with various aspects of the present invention.
Figure 2:
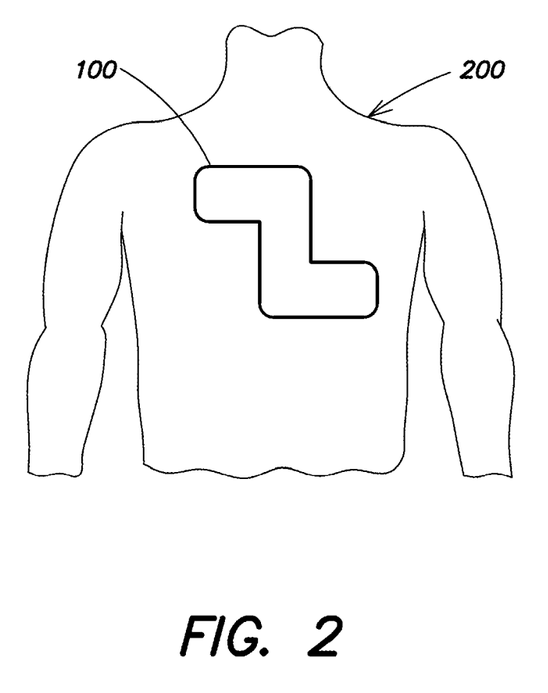
FIG. 2 illustrates the electrode system of FIG. 1 applied to the torso of a subject.

FIG. 1 is a schematic illustration of an electrode system, indicated generally at 100, which may be utilized in an AED device, such as the previously described AED devices available from ZOLL Medical Corporation. As depicted, the electrode system 100 is similar in construction to the CPR-D-padz™ electrode system available from ZOLL Medical Corporation, which may be used with a variety of different defibrillator devices, such as the AED Pro™ defibrillator or the AED Plus™ defibrillator, also from ZOLL Medical Corporation. The electrode system 100 may be placed on or secured to a torso of a subject 200 as illustrated in FIG. 2 to provide treatment, for example, pacing or defibrillation.

As shown in FIG. 1, the electrode system 100 includes a substrate 110, which is indicated in FIG. 1 in dotted lines so as not to obscure the internal components of the electrode system 100 upon which other components of the electrode system are mounted. The substrate may be formed of a fabric, for example, cotton, or a plastic material. The substrate 110 defines a first therapy pad 115, a second therapy pad 125, and a central region defining a compression region 120 that includes a compression sensor 145, such as an accelerometer.

Each therapy pad 115, 125, includes an electrode 130. The electrodes 130 and the compression sensor 145 are electrically coupled via electrical conductors 132, 133, and 147 to a connector 175, which is, in turn, electrically coupled to an AED device 135 through an electrical conductor(s) 140. In certain electrode systems, the electrical conductors 132, 133, and 147 may be designed to be sufficiently long so as to allow the connector 175 to be plugged directly into the AED device 135 without the use of the electrical conductor 140. The AED device 135 is configured to deliver an electrical charge or series of electrical charges to the electrodes 130 as needed. The AED device 135 may be supplied with power from an external source of power or by a battery, capacitor, battery and capacitor, or other electrical energy storage apparatus electrically coupled to the electrode system 100.

When placed on a subject to be treated by cardio pulmonary resuscitation (CPR), the compression region 120 provides a location at which a CPR administrator may apply compressions through the electrode system 100 to the chest of the subject. The compression region 120 of the substrate 110 includes the compression sensor 145, which may monitor the frequency, depth, and intensity of compressions applied to the subject and supply this information to the AED device 135. The AED device 135 may provide feedback, for example, through a speaker or display (not shown), to a CPR administrator based on the information supplied by the compression sensor regarding the sufficiency of the chest compressions or the need to increase or decrease the frequency, depth, or intensity of the compressions.

The electrodes and compression sensor are illustrated in FIG. 1 as formed together in one integrated structure, however, in other electrode systems, the electrodes and/or the compression sensor may be provided on separate and distinct substrates. For example, in the OneStep™ electrode system available from ZOLL Medical Corporation, each defibrillation electrode and the compression device are provided in separate packages and on separate substrates. In still other exemplary electrode systems, such as the Stat-padz™ or Pro-padz™ electrode systems available from ZOLL Medical Corporation, the defibrillation electrodes may be provided in separate packages and on separate substrates, but without any compression sensor. And, in still other electrode systems, electrocardiogram (ECG) sensing electrodes may also be provided, either as separate electrodes electrically coupled to a common connector (e.g., connector 175), or as ECG electrodes integrated into one or both of the therapy pads.

Figure 3:
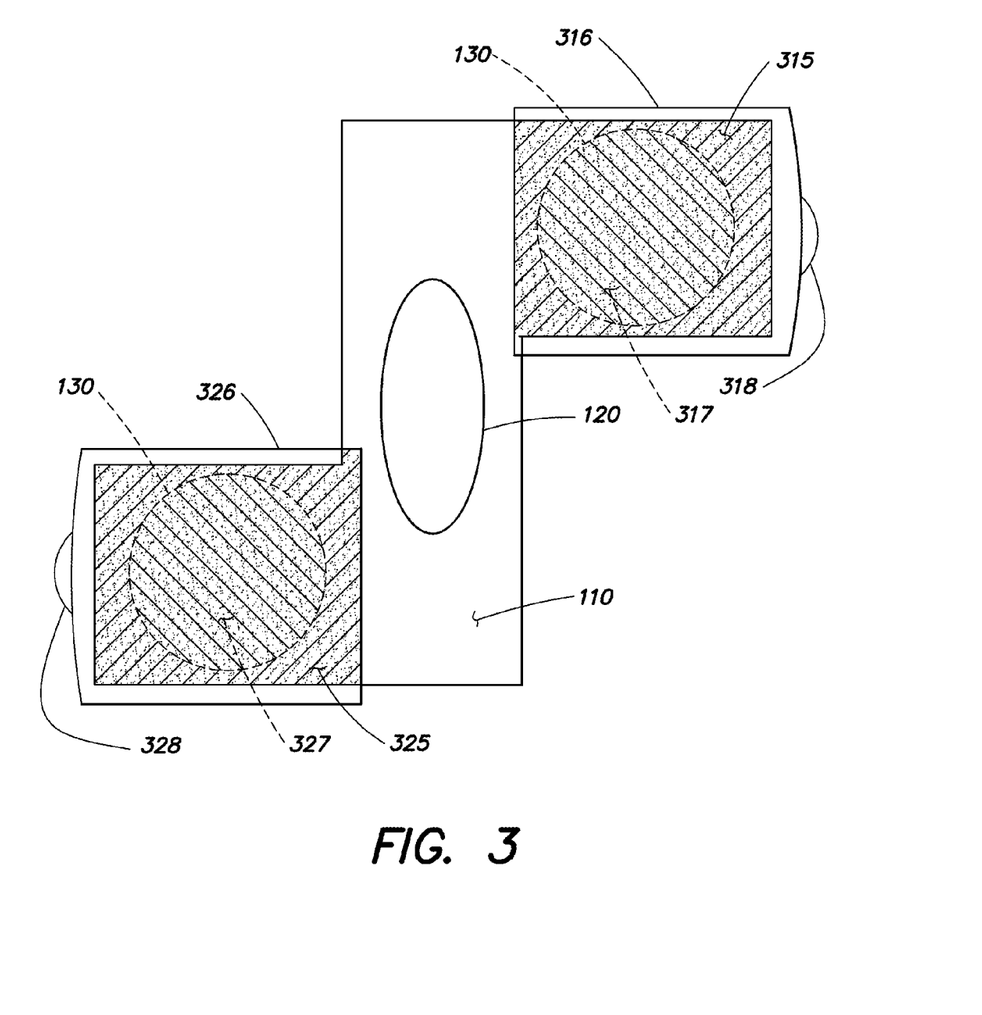
FIG. 3 is a schematic illustration of the electrode system of FIG. 1 from below.

In each of the above-described electrode systems, for convenience and ease of use, the undersurface of the substrate is coated with an adhesive to permit the electrode system to adhere to the skin of the subject. For example, as depicted in FIG. 3 which illustrates the electrode system 100 of FIG. 1 when viewed from below, certain regions 315, 325 of the substrate 110 are coated with an adhesive layer to secure the electrodes 130 to the skin of the subject. The adhesive layer may include any form of adhesive that is capable of securing the electrode to the skin of a subject. In general, the regions 315, 325 surround each respective electrode 130. A gel pad 317, 327 that is typically formed from an electrically conductive and at least somewhat adhesive gel is disposed on the conductive surface of each respective electrode 130. While not visible in FIG. 3, the gel pads 317, 327 generally completely cover the conductive surface of each respective electrode so that there is no direct physical contact between the skin of the subject and the conductive surface of the electrode (i.e., any energy from the electrodes is conducted to the subject's skin through the gel pads). A releasable backing layer 316, 326 covers the adhesive regions prior to use. Although not depicted in FIG. 3, the substrate may also include an adhesive layer formed in the compression region 120 to adhere this region to the skin of the subject, and when present, would be covered by a releasable backing layer prior to use.

In use, the subject would be placed on their back, and the electrode system 100 placed on the body of the subject. Prior to placement, the skin on the torso of the subject may be cleansed with an antiseptic or antiseptic towelette, and the skin of the subject shaved, if necessary. For the electrode system illustrated in FIGS. 1-3, the compression region 120 of the electrode system would typically be positioned first near the sternum of the subject, and then the portions including the electrodes 130. Once appropriately placed on the body of the subject, the releasable backing layers 316, 326 covering the adhesive regions 315, 325 and the gel pads 317, 327 would be removed by pulling on a tab 318, 328 of the releasable backing layers 316, 326. Where the compression region 120 of the substrate 110 includes an adhesive layer and releasable backing layer, the releasable backing layer covering the compression region would typically be removed prior to removal of the releasable backing layers 316, 326. Once removed, pressure would be applied to the central region of each electrode 130 (and the compression region 120, if provided with adhesive) and then radially outward to ensure that each therapy pad (and the compression region 120) conforms as closely as possible to the body of the subject. Once connected to the associated AED device 135, the AED device would monitor the subject's vital signs, and dependent on the type of AED device, prompt the emergency responders appropriately, for example, in the performance of CPR and/or defibrillation or pacing.

As should be appreciated by those skilled in the art, during use, the therapy pads 115, 125 may lose adhesion with the skin of the subject. This is especially true during the performance of chest compressions performed as a part of CPR, as each cycle of compression and relaxation will tend to shear the therapy pads away from the skin of the patient. As the therapy pads lose their adhesion to the skin of the subject, the transthoracic impedance between the electrodes in the therapy pads and the subject increases. Many AED device manufacturers understand this, and some AED devices, such as those available from ZOLL Medical Corporation, include circuitry to sense the transthoracic impedance between the therapy pads and the patient, and to adjust the amount of energy delivered during each defibrillation pulse based upon the sensed transthoracic impedance. For example, various AED devices manufactured by ZOLL Medical Corporation can compensate for changes in the transthoracic impedance between therapy pads and the subject by switching different valued resistors in and out of the energy delivery path. In certain models, the AED device is configured to sense the transthoracic impedance between the therapy pads and the patient, and if the sensed transthoracic impedance exceeds a predetermined value (e.g., 250 Ohms), the AED device issues an alert that one or more of the therapy pads has lost electrical contact with the patient.

Applicants have appreciated that it would be beneficial to monitor changes in the sensed transthoracic impedance between electrodes or therapy pads and the body of a subject over time to identify a loss in contact between the electrodes or therapy pads prior to complete or nearly complete loss of electrical contact. The monitoring may be continuous or nearly continuous and may be used to issue alerts that one or more of the electrodes is losing electrical contact and should be re-adhered or replaced. Although this aspect of the present invention is described primarily with respect to defibrillation electrodes or defibrillation therapy pads, it should be appreciated that aspects of the present invention are applicable to any electrode that is placed on the skin of a subject, irrespective of whether the electrode is an electrode with an adhesive backing, or is a non-adhesive electrode that is held against the patient's skin by some other mechanism, and irrespective of the type of electrode (e.g., an ECG sensing electrode, a defibrillation electrode, a combined ECG sensing/defibrillation electrode, a cardiac pacing electrode, a multi-segment electrode, or any other type of electrode capable of sensing a physiological parameter of the subject (e.g., pulse oxygen level, thoracic transthoracic impedance, pulse rate, etc.)

Figure 4:
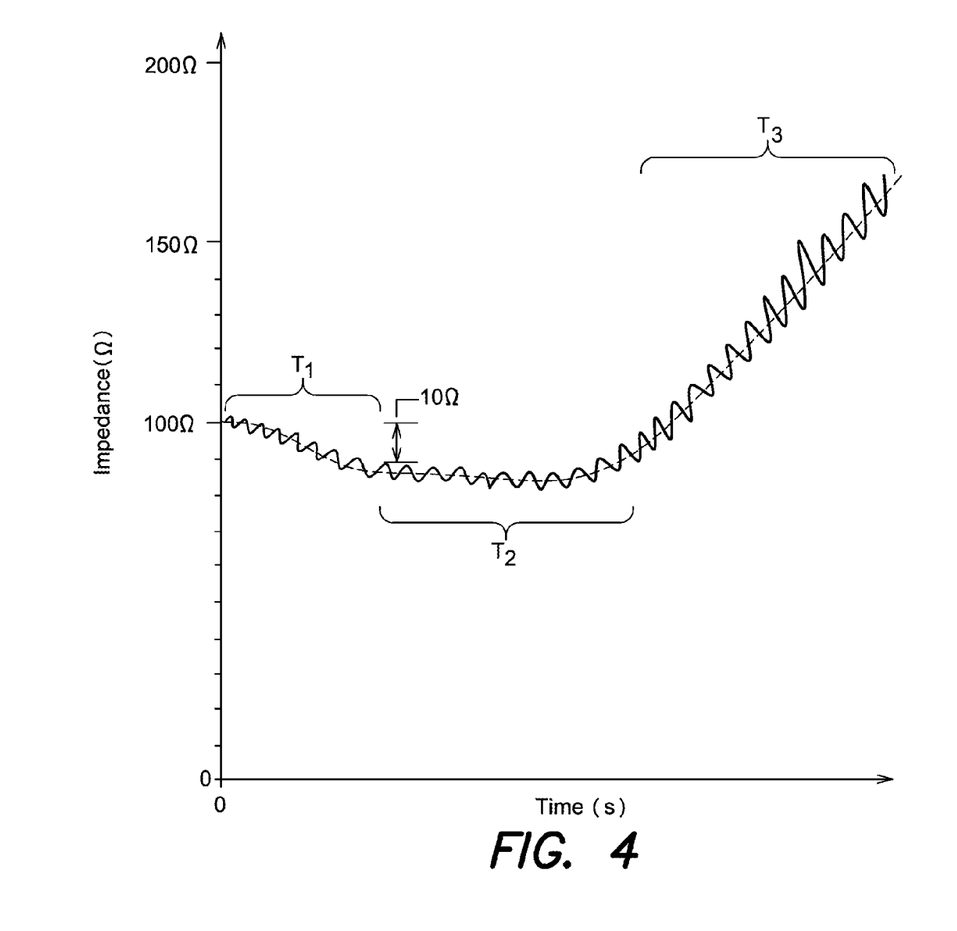
FIG. 4 is a waveform diagram illustrating the manner in which the transthoracic impedance measured between a pair of electrodes may change over time during the performance of CPR compressions.

FIG. 4 is a waveform diagram illustrating the manner in which the transthoracic impedance measured between a pair of electrodes that are adhered to a subject's body may change over time during the performance of CPR chest compressions. The CPR compressions may be performed manually, for example, by an emergency responder manually compressing the subject's chest, or they may be performed mechanically, for example by a load distributing constricting band type of mechanical compression device, such as the AutoPulse™ Non-Invasive Cardio Support Pump manufactured by ZOLL Medical Corporation, a piston driven mechanical compression device with active decompression, such as the Lucas™ Chest Compression System, manufactured by Physio-Control International, Inc., etc.

In FIG. 4, the low frequency value of the transthoracic impedance is represented in dashed line form, and the actual high frequency waveform is represented in solid line form. The sinusoidal variation in the high frequency waveform is primarily due to, and correlated with, CPR chest compressions. During the performance of CPR chest compressions, the sensed transthoracic impedance may vary by about 1 to 15 Ohms in response to the performance of chest compressions, dependent on the phase of the chest compressions, with a lower transthoracic impedance typically reflecting the compression phase of a compression cycle. Although not shown in FIG. 4, superimposed on the high frequency waveform may be a variation in transthoracic impedance based upon the subject's breathing (e.g., a variation of approximately 1 Ohm or less), and heartbeat (e.g., a variation of approximately ½ Ohm or less), if present. It should be appreciated that although the transthoracic impedance values depicted in FIG. 4 are representative of what would be seen over a broad range of different subjects, these values will, of course, vary from subject to subject.

As depicted in FIG. 4, when the electrodes are first placed upon the body of the subject (i.e., at Time=0), the transthoracic impedance that is sensed between the electrodes (and including the body of the subject) is approximately 100 Ohms. This transthoracic impedance value is typical for properly placed electrodes, although it should be appreciated that the transthoracic impedance value may vary from subject to subject. The transthoracic impedance that is sensed between the electrodes then decreases by approximately 10 Ohms as the outermost layer of skin (i.e., the stratum corneum) of the subject moistens and becomes more conductive due to the presence of the gel pad. This period where the transthoracic impedance decreases due to the moistening of the stratum corneum is designated $T_1$ in FIG.

4. Following period $T_1$, the transthoracic impedance that is sensed between the pads remains relatively constant, as depicted in the period designated $T_2$. Following the period $T_2$, the transthoracic impedance that is sensed between the electrodes may increase to and beyond 150 Ohms, as indicated by the period of time designated $T_3$, due to the repeated application of CPR compressions. If nothing is done to re-adhere the electrode(s) to the skin of the subject, electrical contact between the electrodes and the patient will be lost, with many AED devices declaring that contact between the electrode(s) and the skin of the subject has been lost at a transthoracic impedance value of approximately 250 Ohms or more.

Figure 5:
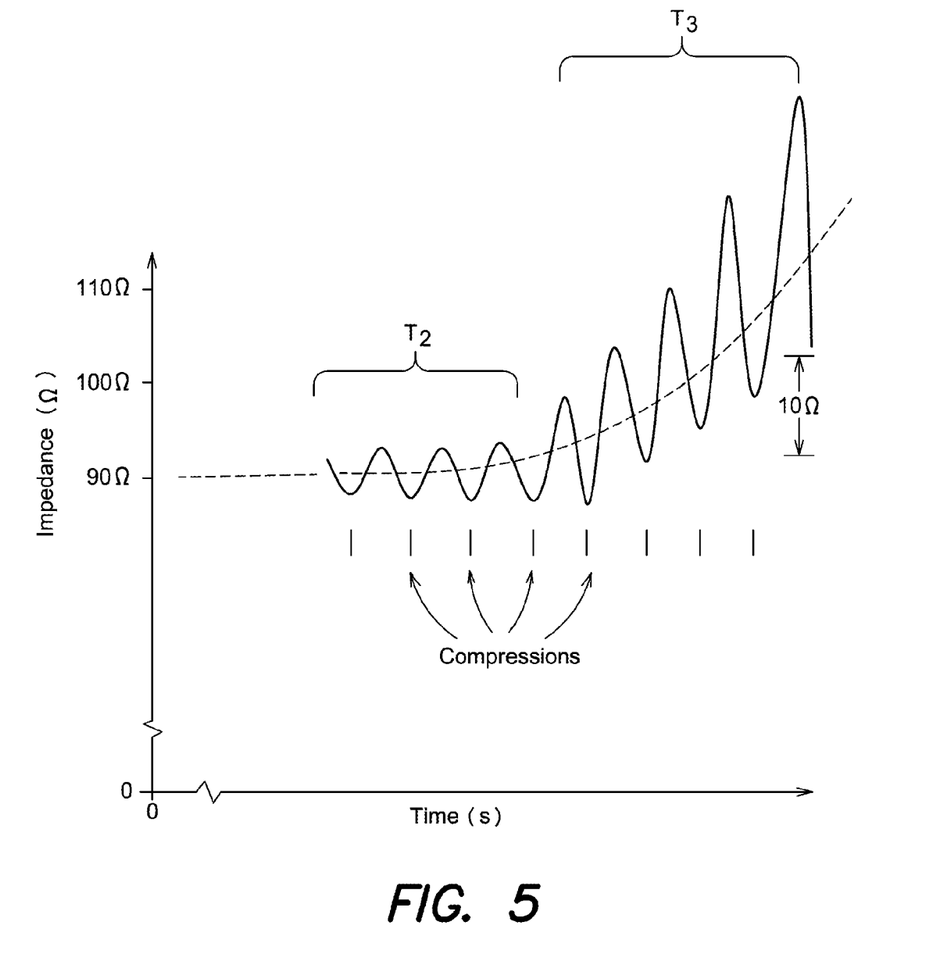
FIG. 5 is an expanded version of the waveform diagram of FIG. 4 showing the manner in which the transthoracic impedance measured between the pair of electrodes may change as the electrodes lose electrical contact with the subject's skin.

FIG. 5 is an expanded waveform diagram illustrating the manner in which the transthoracic impedance measured between a pair of electrodes that are adhered to a subject's body may change over time during the performance of CPR chest compressions during the periods $T_2$ and $T_3$ previously described with respect to FIG. 4. As in FIG. 4, the low frequency value of the transthoracic impedance (e.g., at frequencies below a set frequency, such as 0.5 Hz, 0.1 Hz, or 0.05 Hz, that is below the frequency of chest compressions) is represented in dashed line form, and the actual high frequency waveform (e.g., at frequencies at or above the set frequency) is represented in solid line form. In FIG. 5, variations in the high frequency waveform due to the subject's breathing and/or heartbeat, if present, are not depicted. As previously described, during the performance of CPR compressions, the sensed high frequency transthoracic impedance may vary by about 1 to 15 Ohms in response to the performance of chest compressions, dependent on the phase of the chest compressions.

During the period $T_3$ depicted in FIG. 5, the amplitude of the low frequency component of the transthoracic impedance signal increases by more than approximately 10 Ohms, and this change in amplitude of the low frequency component may be monitored and compared to a threshold to detect that the electrode(s) is/are beginning to lose electrical contact with the subject's skin. The threshold may be set to any convenient value and may vary dependent upon the capabilities of the AED device. For example, where the AED device is able to compensate for changes in transthoracic impedance over a range of transthoracic impedance values, the threshold may be set to one half or one third this range. The present low frequency value of the transthoracic impedance signal may be compared to the lowest sensed transthoracic impedance value, and if the difference is more than that threshold, the AED device may signal an alert that one or more of the electrodes is beginning to lose electrical contact with the subject's skin.

During the portion of period $T_2$ depicted in FIG. 5, the amplitude of the high frequency component of the transthoracic impedance signal is approximately 8 Ohms, but this amplitude increases during the period $T_3$ due to the electrode(s) losing electrical contact with the subject's skin. This change in amplitude of the high frequency component of the transthoracic impedance signal may also be monitored and used to detect that the electrode(s) is/are beginning to lose electrical contact with the subject's skin. For example, the amplitude of the high frequency component of the transthoracic impedance signal may be compared to a threshold, or the change in the amplitude of the high frequency component of the transthoracic impedance signal compared to a threshold and used to detect the loss of electrical contact. As further illustrated in FIG. 5, the shape of the high frequency waveform, as well as the slope of the high frequency component of the transthoracic impedance signal also changes during period $T_3$, and these changes may also be monitored and used to detect that the electrode(s) is/are beginning to lose electrical contact with the patient's skin.

Figure 6:
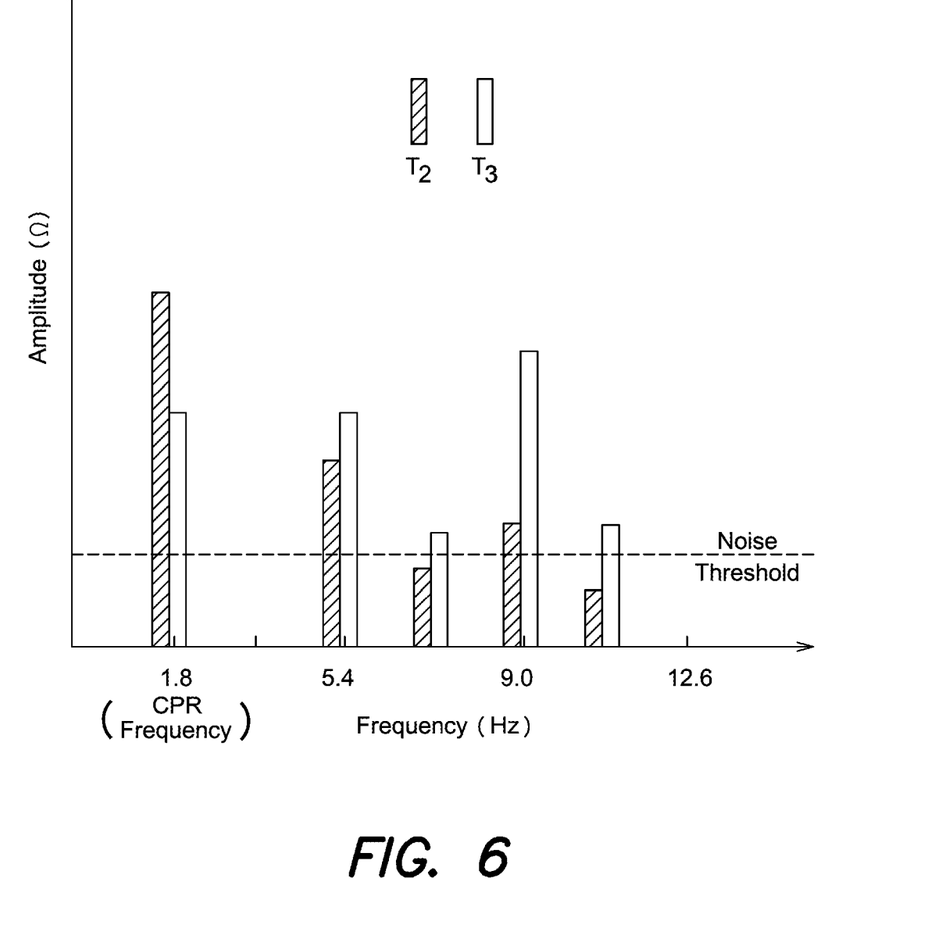
FIG. 6 is illustrates spectral components of the transthoracic impedance signal shown in FIG. 4 during the periods $T_2$ and $T_3$.

In addition to monitoring the amplitude, shape, or slope of the high frequency component of the transthoracic impedance signal, a spectral analysis of the transthoracic impedance signal may also be used to detect that one or more of the electrodes is beginning to lose electrical contact with the subject's skin. For example, FIG. 6 is a spectral diagram illustrating the amplitude and the frequency of the transthoracic impedance signal depicted in FIG. 4 during the periods $T_2$ and $T_3$, with period $T_2$ being depicted in cross-hatch. As can be seen in FIG. 6, during the period $T_2$, the amplitude of the transthoracic impedance signal at the fundamental frequency (i.e., the frequency at which CPR chest compressions are performed, in this example 1.8 Hz) is significantly larger than the amplitude at the third (5.4 Hz) and fifth (9.0 Hz) harmonics, with the amplitude at the third harmonic being greater than that of the fifth harmonic. This is in contrast to the amplitudes at those same frequencies during period $T_3$ in which one or more electrodes are losing electrical contact with the subject's skin, where the amplitude at the third harmonic is greater than the amplitude at the fundamental frequency, and the amplitude of the fifth harmonic is greater than that of the third harmonic. As also depicted in FIG. 6, during the period $T_3$ where the one or more electrodes are losing electrical contact with the subject's skin, noise at frequencies other than the fundamental frequency and the third and fifth harmonics is greater than a noise threshold established during the period $T_2$. In accordance with an aspect of the present invention, the relative energy content at the fundamental frequency of CPR chest compressions and its harmonics may be compared to one another, and/or to a determined baseline level of noise to detect that one or more of the electrodes is losing electrical contact with the skin of the subject.

Figure 7:
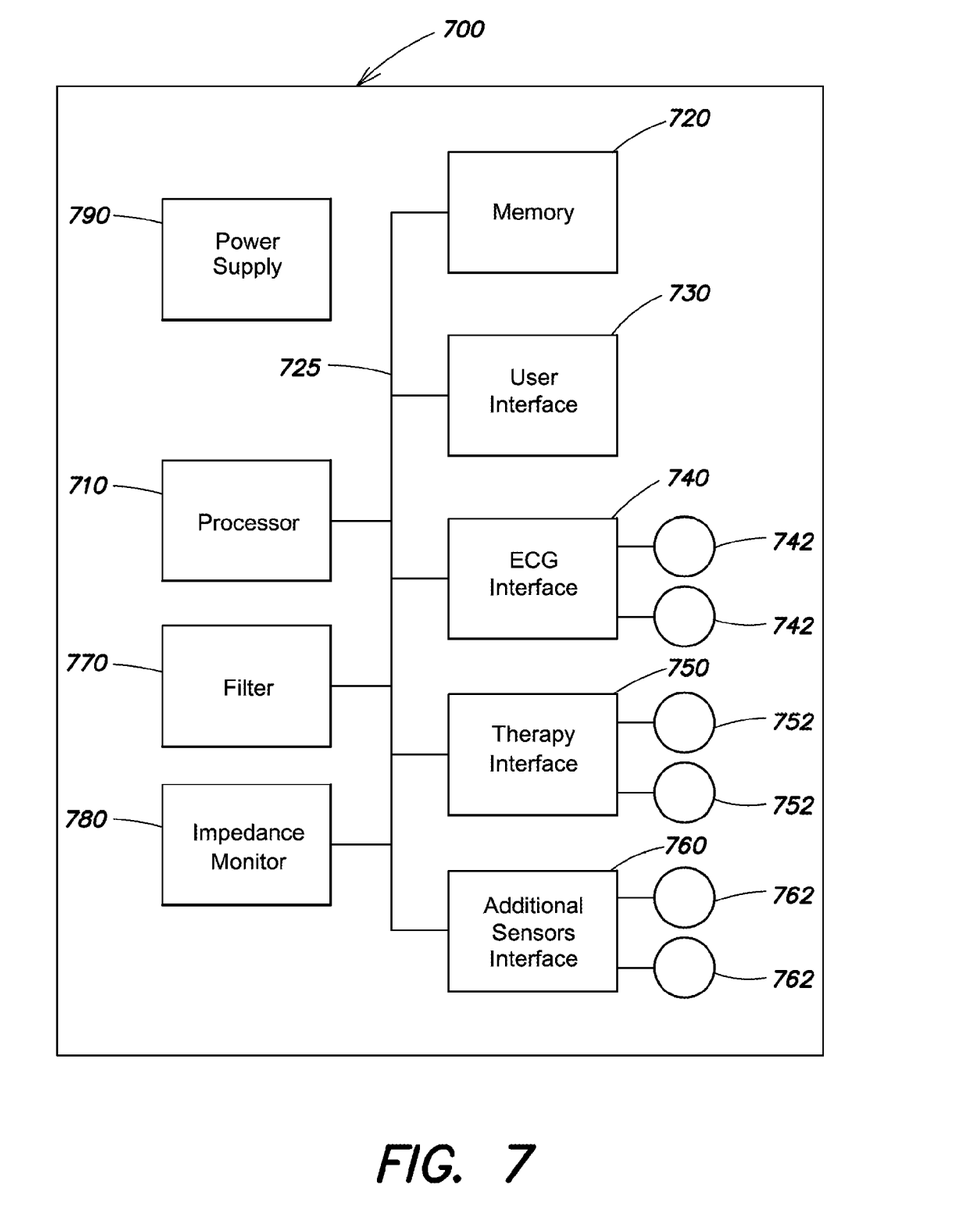
FIG. 7 is a schematic illustration of a life support device, such an AED in accordance with an embodiment of the present invention.

FIG. 7 is a block diagram of a life support device 700 that may be used to monitor transthoracic impedance in accordance with aspect of the present invention. The life support device 700 may be a Basic Life Support (BLS) device, such as a BLS defibrillator device, or an Advanced Life Support (ALS) device, such as an Automated External Defibrillator (AED) device and/or pacing device.

As illustrated in FIG. 7, the life support device 700 includes at least one processor 710, a memory 720, a user interface 730, an ECG interface 740, a therapy interface 750, an additional sensors interface 760, a transthoracic impedance filter 770, and a transthoracic impedance monitor 780 coupled to one another via, for example, a bus 725. A power supply 790, which may include a low frequency power supply, such as one or more batteries, or a high frequency power supply, provides power to the various components of the life support device 700. Although not depicted, the life support device 700 would typically include a communication network interface by which the device could communicate with other devices, or with health care professionals, such as a hospital or other emergency care providers via a wired or wireless communication network.

The at least one processor 710 is typically a commercially available general purpose processor or a digital signal processor, such as a processor manufactured by Texas Instruments, Intel, Motorola, AMD, Sun, IBM, Motorola, Freescale and ARM Holdings. However, the at least one processor 710 may be any type of processor, multiprocessor or controller, whether commercially available or specially manufactured. The at least one processor 710 is configured to monitor the subject's medical condition, to perform medical data logging and storage, and/or to provide medical treatment to the subject in response to a detected medical condition, such as cardiac arrhythmia.

The memory 720 includes a non-transitory computer readable and writeable nonvolatile data storage medium configured to store non-transitory instructions and other data. In addition, the memory includes a processor memory that stores data during operation of the at least one processor 710. In some examples, the processor memory includes a relatively high performance, volatile, random access memory such as dynamic random access memory (DRAM), static memory (SRAM) or synchronous DRAM. In general, the memory may include any device for storing data, as embodiments of the present invention are not limited to a particular memory, memory system or data storage system.

The user interface 730 includes a combination of hardware and software (and/or firmware) components that allow the at least one processor 710 to communicate with an external entity, such as a user. These components are configured to receive information from actions such as physical movement, verbal intonation or thought processes. In addition, the components of the user interface 730 can provide information to external entities. Examples of the components that may be employed within the user interface 730 include keyboards, LEDs, mouse devices, trackballs, microphones, touch screens, printing devices, display screens and speakers.

The ECG interface 740 includes a combination of hardware and software (and/or firmware) components that allow the at least one processor 710 to communicate with a plurality of electrocardiogram (ECG) sensing electrodes 742 configured to monitor the ECG of a subject. The therapy interface 750 includes a combination of hardware and software (and/or firmware) components that couple one or more therapy delivery devices, such as capacitors and therapy electrodes 752 for defibrillation and/or pacing, to the at least one processor 710. In addition to providing electrical therapy to a subject, the therapy interface is capable of transmitting an electrical signal into the body of the subject that may be received by another electrode (e.g., another therapy electrode or an ECG sensing electrode) and used to measure transthoracic impedance. For example, the electrical signal used to measure transthoracic impedance may have a frequency in the range of approximately 50 to 100 kHz and a current of approximately 0.5 to 4 mA RMS, as described in Chapter 75 of the Biomedical Engineering Handbook, First Edition, CRC Press, Editor-in-Chief Joseph D. Bronzino, ©1995. It should be appreciated that in certain life support devices in which the therapy pads include ECG sensing electrodes as well as therapy electrodes, or where the therapy electrodes are also capable of being used to monitor the ECG of a subject, the ECG interface and the therapy interface may be combined into a single interface.

The additional sensors interface 760 may include a combination of hardware, software, and/or firmware to couple the at least one processor 710 to one or more other sensors 762, such as body temperature sensors, respiration sensors, blood pressure sensors, thoracic transthoracic impedance sensors, pulse oxygen level sensors, heart sound sensors, accelerometers or compression sensors, etc. For example, where the life support device 700 is used in combination with an electrode system that includes a compression sensor (e.g., the compression sensor 145 in FIG. 1), the compression sensor may be electrically coupled to the at least one processor 710 via the additional sensors interface 760 to accurately identify the frequency of CPR compressions, the depth or velocity of CPR chest compressions, or the frequency, depth, and velocity of CPR chest compressions. Alternatively, where a mechanical compression device is used, an output signal from the mechanical compression device that is indicative of the frequency, depth, and/or velocity of mechanical CPR compressions may be electrically coupled to the additional sensors interface 760 to accurately identify the frequency, depth, and/or velocity of CPR compressions.

In accordance with an aspect of the present invention, the life support device 700 also includes a transthoracic impedance filter 770 and a transthoracic impedance monitor 780. In accordance with one aspect of the present invention, the transthoracic impedance filter 770 may be used to filter a transthoracic impedance signal indicative of the transthoracic impedance detected between pairings of electrodes, such as between pairs of therapy electrodes, pairs of ECG sensing electrodes, etc. For example, the transthoracic impedance filter may be configured as a band pass filter where the pass bands correspond to the fundamental frequency of CPR chest compressions and its harmonics. The fundamental frequency of the CPR chest compressions may be identified based upon a signal from a chest compression device 145 (FIG. 1), such an accelerometer, from an output signal indicative of the frequency of CPR compressions provided by a mechanical compression device, or based upon a frequency analysis of the transthoracic impedance signal in which the fundamental frequency corresponds to the frequency of chest compressions, or combinations thereof.

In accordance with an aspect of the present invention, the transthoracic impedance monitor 780 is configured to monitor both low frequency and high frequency components of the transthoracic impedance signal. For example, the transthoracic impedance monitor can continuously or nearly continuously monitor a low frequency value of the transthoracic impedance signal, compare it to a threshold, and in response to a low frequency value of the transthoracic impedance signal meeting or exceeding the threshold, alert the at least one processor 710. The at least one processor may then issue an audio alert, a video alert, or both to inform an emergency responder that one or more of the electrodes is beginning to lose electrical contact with the subject. The transthoracic impedance monitor 780 can also continuously or nearly continuously monitor high frequency components of the transthoracic impedance signal in both the time domain and the frequency domain to detect that one or more electrodes is beginning to lose electrical contact, and to alert the at least one processor. The transthoracic impedance monitor may also correlate high frequency components of the transthoracic impedance signal with a signal indicative of the frequency of CPR chest compressions, the depth or velocity of CPR chest compressions, or the frequency, depth, and velocity of CPR chest compressions, such as an external signal received from a chest compression sensor or a mechanical chest compression device, or an internal signal that is based on an analysis of the transthoracic impedance signal itself.

Although the transthoracic impedance filter 770 and the transthoracic impedance monitor 780 are illustrated in FIG. 7 as being distinct from the at least one processor 710, it should be appreciated that in certain embodiments, these components may be implemented in code or as a process that is executed by the at least one processor 710.

Figure 8:
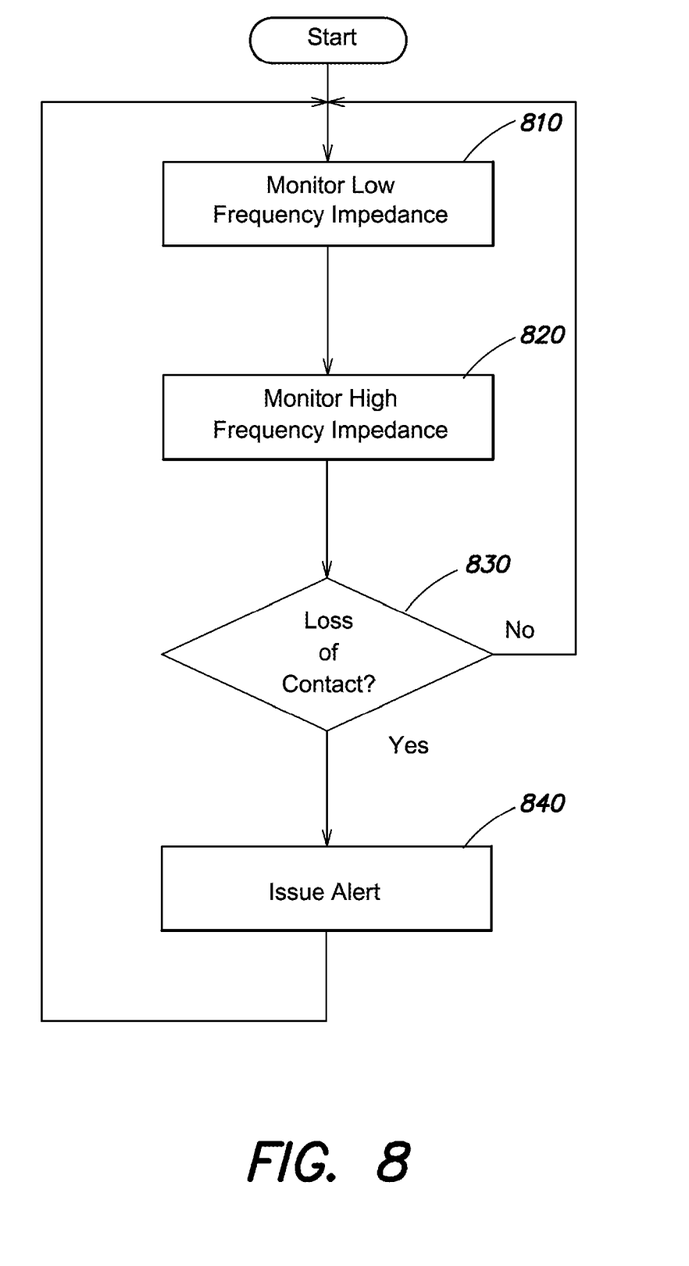
FIG. 8 is a flowchart of a transthoracic impedance monitoring routine in accordance with an aspect of the present invention.

FIG. 8 is a flowchart of a transthoracic impedance monitoring routine that may be performed by a life support device, or a transthoracic impedance monitor of a life support device, such as the life support 700 described above with respect to FIG. 7. In act 810, the transthoracic impedance monitoring routine monitors the low frequency value of the transthoracic impedance measured between pairings of electrodes, for example, between the pairing of therapy electrodes 752. For example, during act 810, the transthoracic impedance monitoring routine may continuously or substantially continuously measure and store the low frequency value of transthoracic impedance at frequencies below a set frequency that is below the frequency of CPR chest compressions. Where the measured low frequency value of transthoracic impedance is lower than previously measured values, the monitoring routine may additionally store that measured low frequency value as being indicative of the lowest measured low frequency value of transthoracic impedance. Referring back to FIG. 4, during the period of time $T_1$, the lowest measured low frequency value of transthoracic impedance would progressively decrease by about 10 Ohms until it remained at a substantially steady value during period $T_2$. The monitoring routine would continue to measure and store the current low frequency value of transthoracic impedance during the transition from period $T_2$ to $T_3$, with the currently measured low frequency value of the transthoracic impedance increasing during this transition into period $T_3$. In act 830 (described more fully below), the difference between the current measured low frequency value of the transthoracic impedance and the stored lowest measured low frequency value (e.g., the baseline value established during period $T_2$) may be compared to a predetermined threshold that is indicative of one or more of the electrodes losing electrical contact with the skin of the subject.

In act 820, the transthoracic impedance monitoring routine monitors parameters relating to the high frequency components of the transthoracic impedance signal at frequencies at and above the set frequency and including the frequency of CPR chest compressions. Parameters that may be monitored during act 820 include the amplitude of the high frequency waveform, the slope of the high frequency waveform, the shape of the high frequency waveform, and spectral characteristics of the high frequency waveform. For example, during act 820, the transthoracic impedance monitoring routine may continuously or substantially continuously determine and store the amplitude of the high frequency waveform, the slope of the high frequency waveform, the shape of the high frequency waveform, and/or a spectral analysis of the high frequency waveform such, as the amount of energy of the high frequency waveform at the fundamental frequency of CPR compressions and harmonics thereof, as well as an energy level of background noise. In addition, in act 820, one or more of the parameters relating to the high frequency components of the transthoracic impedance signal may be correlated with a signal indicative of the frequency, depth, or velocity of CPR chest compressions to identify changes indicative of a loss of electrical contact with the skin of the subject. A more detailed description of the various parameters relating to the high frequency components of the transthoracic impedance signal that may be monitored in act 820 is discussed with respect to FIG. 9 below.

In act 830, the transthoracic impedance monitoring routine makes a determination as to whether more currently measured values of the low frequency transthoracic impedance and/or the more currently determined parameters of the high frequency transthoracic impedance indicate that one or more of the electrodes is starting to lose electrical contact with the skin of the subject. In response to a determination that the more currently measured values of the low frequency transthoracic impedance and the more currently determined parameters of the high frequency transthoracic impedance do not indicate that one or more of the electrodes is starting to lose electrical contact with the skin of the subject, the monitoring routine returns to act 810 where acts 810, 820, and 830 are repeated. Alternatively, in response to a determination in act 830 that more currently measured values of the low frequency transthoracic impedance, more currently determined parameters of the high frequency transthoracic impedance, or both indicate that one or more of the electrodes is starting to lose electrical contact with the skin of the subject, the monitoring routine proceeds to act 840.

In act 840, the transthoracic impedance monitoring routine issues an alert to the at least one processor 710 that one or more of the electrodes is starting to lose electrical contact with the skin of the subject. In response to receiving the alert, the at least one processor may issue a visual alert, an audio alert, or both an audio and a visual alert to a user of the life support device via the user interface 730. The alert may, for example, inform the user that one or more of the electrodes is losing contact with the subject's skin. The alert may alternatively or additionally instruct the user to check whether the electrodes are appropriately adhered to the subject's skin, instruct the user to apply pressure to each of the electrodes to re-adhere them to the subject's skin, or instruct the user to replace the electrodes with a new set of electrodes if such is possible. After issuing the alert in act 840, the transthoracic impedance monitoring routine may return to act 810, wherein acts 810, 820, 830, and 840 may be repeated. It should be appreciated by those skilled in the art that acts 810 and 820 need not be performed in the order shown in FIG. 8, as act 820 may alternatively be performed prior to act 810. Moreover, it should be appreciated that dependent on the capabilities of the life support device 700, the life support device may only be capable of monitoring the low frequency value of transthoracic impedance, such that act 820 may be omitted.

Figure 9:
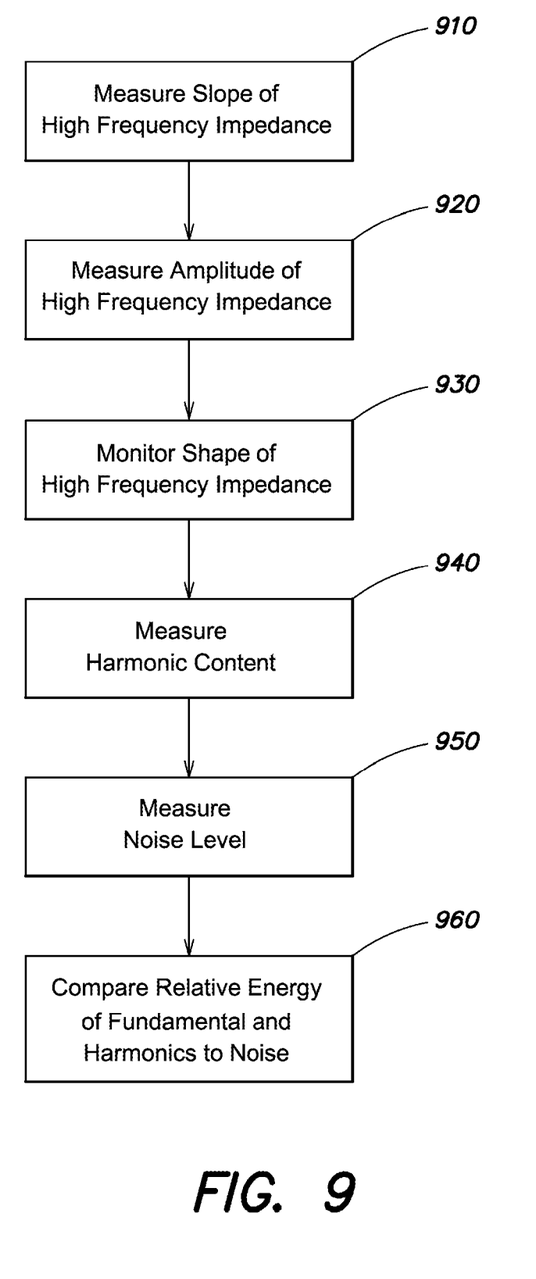
FIG. 9 illustrates various acts that may be performed to monitor the high frequency transthoracic impedance during the transthoracic impedance monitoring routine of FIG. 8.

FIG. 9 is a flowchart of various acts that may be performed by the transthoracic impedance monitoring routine of FIG. 8 to monitor the high frequency transthoracic impedance during act 820. It should be appreciated by those skilled in the art that the order in which these acts are performed may be changed, and that, in certain embodiments, certain acts may be omitted, dependent on the capabilities of the life support device. For example, where the life support device is incapable of performing a spectral analysis of the high frequency transthoracic impedance waveform, those acts dependent upon such a spectral analysis may be omitted.

In act 910 the transthoracic impedance monitoring routine continuously or substantially continuously measures the slope of the high frequency transthoracic impedance waveform and stores the measured slope for comparison (e.g., in act 830 of FIG. 8) with previously measured values. For example, where the currently measured slope is lower than previously measured values, the monitoring routine may additionally store that slope value as being indicative of the lowest measured slope value (e.g., a baseline slope value). Alternatively, the transthoracic impedance monitoring routine may determine an average or a running average of the slope of the high frequency waveform, for example, over a predetermined number of CPR chest compressions, and store that average or running average for comparison (e.g., in act 830) with more currently measured slope values. Where the comparison indicates that the current slope of the high frequency waveform is appreciably greater than the lowest measured slope value, the average, or the running average, the transthoracic impedance monitoring routine may determine that one or more of the electrodes is losing electrical contact with the skin of the subject (e.g., act 830 Yes).

In act 920, the transthoracic impedance monitoring routine continuously or substantially continuously measures the amplitude of the high frequency transthoracic impedance waveform and stores the measured amplitude for comparison (e.g., in act 830) with previously measured values. For example, where the currently measured amplitude of the high frequency transthoracic impedance waveform is lower than previously measured values, the monitoring routine may additionally store that measured amplitude as being the lowest measured amplitude value (e.g., a baseline amplitude value). Alternatively, the transthoracic impedance monitoring routine may determine an average or a running average of the amplitude of the high frequency transthoracic impedance waveform, for example over a predetermined number of CPR chest compressions, and store that average or running average for comparison (e.g., in act 830) with more currently measured values. Where the comparison indicates that the current amplitude of the high frequency waveform is appreciably greater than the lowest measured amplitude value, the average, or the running average, the transthoracic impedance monitoring routine may determine that one or more of the electrodes is losing electrical contact with the skin of the subject (e.g., act 830 Yes).

In act 920, the transthoracic impedance monitoring routine may also correlate the amplitude of the high frequency transthoracic impedance waveform, or changes in the amplitude of the high frequency transthoracic impedance waveform to a signal indicative of the frequency of CPR chest compressions, for example from a compression sensor or a mechanical compression device. Where the electrodes are in good electrical contact with the skin of the subject, one would expect the amplitude of the high frequency transthoracic impedance waveform to decrease during the compression phase of CPR chest compressions due to a decrease in lung volume and decreases in the volume of blood in the heart, peripheral arties and veins, and to increase during the relaxation phase of CPR chest compressions. Where the amplitude of the high frequency transthoracic impedance waveform does not decrease as much during the compression phase as previously measured values, or where the amplitude of the high frequency transthoracic impedance waveform increases during the compression phase relative to previously measured values, the transthoracic impedance monitoring routine may determine that one or more of the electrodes is losing electrical contact with the skin of the subject. (e.g., act 830 Yes).

Figure 10:
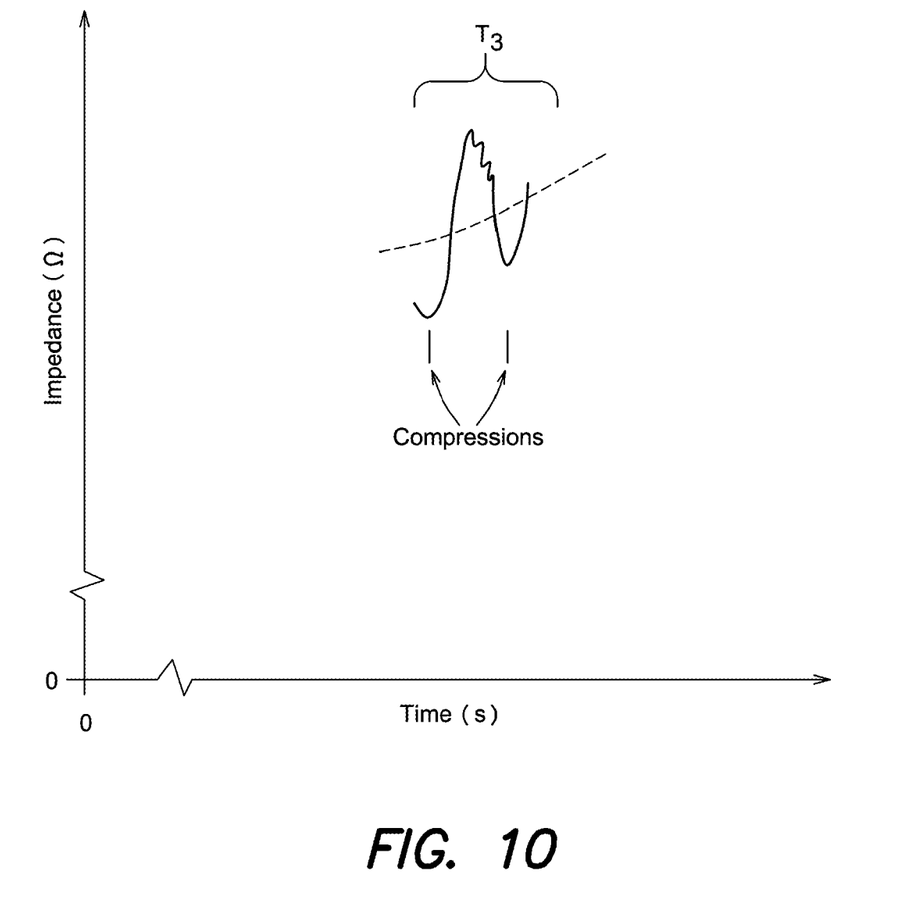
FIG. 10 is an expanded waveform diagram showing the manner in which the transthoracic impedance measured between the pair of electrodes may change as the electrodes lose electrical contact with the subject's skin during a compression phase of CPR compressions.

In act 930, the transthoracic impedance monitoring routine continuously or substantially continuously monitors the shape of the high frequency transthoracic impedance waveform and stores the monitored shape for comparison (e.g., in act 830) with previously measured values. For example, in act 930, the transthoracic impedance monitoring routine may determine an equation that most closely approximates the shape of the high frequency waveform and store that equation as being indicative of the shape of the high frequency waveform. Where an equation corresponding to the shape of the currently measured high frequency waveform differs by more than a determined amount from that of the previously determined equation, the transthoracic impedance monitoring routine may determine that one or more of the electrodes is losing electrical contact with the skin of the subject (e.g., act 830 Yes). In act 930, the transthoracic impedance monitoring routine may also correlate the shape of the high frequency transthoracic impedance waveform, or changes in the shape of the high frequency transthoracic impedance waveform to a signal indicative of the frequency of CPR chest compressions. Where the electrodes are in good electrical contact with the skin of the subject, one would expect the shape of the high frequency transthoracic impedance waveform to have a relatively smooth sinusoidal shape. However, where one or more of the electrodes is losing electrical contact with the skin of the subject, the shape of the high frequency transthoracic impedance waveform may show a stepped shape during the compression phase of CPR chest compressions as one or more of the electrodes shears away from electrical contact with the skin of the subject, such as depicted in the expanded waveform diagram of FIG. 10. Where the shape of the high frequency transthoracic waveform changes during the compression phase relative to previous compressions, the transthoracic impedance monitoring routine may determine that one or more of the electrodes is losing electrical contact with the skin of the subject. (e.g., act 830 Yes).

In act 940, the transthoracic impedance monitoring routine measures the energy content of the high frequency transthoracic impedance waveform at a number of different frequencies corresponding to the fundamental frequency of the CPR chest compressions and harmonics thereof. The fundamental frequency of the CPR compressions may be determined based on the high frequency transthoracic impedance waveform itself, or based on a signal indicative of the frequency of CPR chest compressions, such as from a chest compression sensor or a mechanical chest compression device. The harmonics may include both odd and even harmonics of the fundamental frequency, and the transthoracic impedance monitoring routine may use the transthoracic impedance filter 770 (FIG. 7) to filter out other frequencies. For example, during the period $T_2$, the transthoracic impedance monitoring routine may measure and store the energy level at the fundamental frequency of CPR chest compressions as well as the relative energy level of each harmonic. These amounts of energy (e.g., baseline values) may be compared with more currently measured values. Where the energy content of more currently measured values differs from that determined during period $T_2$, or where the relative energy level at the fundamental frequency and various harmonics of more currently measured values differ from those obtained during period $T_2$, the transthoracic impedance monitoring routine may determine that one or more of the electrodes is losing electrical contact with the skin of the subject (e.g., act 830 Yes).

In act 950, the transthoracic impedance monitoring routine measures the energy level of background noise. For example, during the period $T_2$, the transthoracic impedance monitoring routine may measure and store the energy level of background noise at frequencies other than the fundamental frequency of CPR chest compressions. This level of noise (e.g., baseline value of noise) may be compared with more currently measured values. Where more currently measured values of noise differ from those determined during the period $T_2$, the transthoracic impedance monitoring routine may determine that one or more of the electrodes is losing electrical contact with the skin of the subject (e.g., act 830 Yes).

In act 960, the transthoracic impedance monitoring routine may compare the relative energy content at the fundamental frequency of CPR chest compressions and its harmonics (for example, as measured during act 940) relative to the energy level of noise (for example, as measured during act 950) during period $T_2$ with more currently measured values to determine whether that ratio has changed. Where it is determined that the ratio of the energy level at the fundamental frequency and its harmonics has changed, the transthoracic impedance monitoring routine may determine that one or more of the electrodes is losing electrical contact with the skin of the subject (e.g., act 830 Yes).

It should be appreciated that the various threshold values described with respect to FIGS. 8 and 9 may vary dependent upon whether the CPR chest compressions are performed manually, or with the aid of a mechanical chest compression device. For example, where the CPR chest compressions are performed by a mechanical chest compression device, the thresholds may be smaller than those used during manual CPR chest compressions, as the CPR chest compressions delivered by a mechanical chest compression device are likely to be more uniform in terms of frequency, rate (e.g., velocity) of compression and relaxation, depth of compression, etc. than those applied manually. In some embodiments, the transthoracic impedance monitoring routine may be configured to use different thresholds dependent on whether the CPR compressions are performed manually or with the aid of a mechanical chest compression device. For example, an initial determination could be made prior to act 810 in FIG. 8 as to whether the CPR chest compressions were being performed manually or with the aid of a mechanical chest compression device. This determination could be made empirically by the transthoracic impedance monitor based upon the regularity of the chest compressions exhibited in the transthoracic impedance signal, or could be based on a response to a query provided by the user interface of the life support device asking the user of the device whether the compressions are to be provided manually or mechanically.

It should be appreciated that by monitoring changes in the transthoracic impedance sensed between pairing of electrodes during CPR, the loss of electrical contact between the electrodes and the skin of the subject may be detected prior to a complete loss of electrical contact. Although such early detection of the loss of electrical contact is particularly important with respect to electrodes used to provide electrical therapy, such as defibrillation or pacing, it may also be used to identify when other electrodes, such as ECG sensing electrodes, are beginning to lose electrical contact.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

What is claimed is:

1. A life support device, comprising:
a pair of electrodes configured to be attached to a skin of a subject;
a therapy interface electrically coupled to the pair of electrodes; and
a transthoracic impedance monitor electrically coupled to the therapy interface, the transthoracic impedance monitor being configured
to monitor transthoracic impedance parameters of a transthoracic impedance signal between the pair of electrodes over time, wherein the transthoracic impedance signal has a high frequency waveform component that varies with a frequency of CPR chest compressions, and wherein the transthoracic impedance parameters include at least one of a slope of the high frequency waveform component of the transthoracic impedance signal, a shape of the high frequency waveform component of the transthoracic impedance signal, and a relative energy content of the high frequency waveform component of the transthoracic impedance signal at a fundamental frequency of the transthoracic impedance signal and/or at a harmonic of the fundamental frequency of the transthoracic impedance signal,
to establish baseline levels of the transthoracic impedance parameters,
to detect whether changes over time in at least one transthoracic impedance parameter exceeds a corresponding baseline level by a threshold,
to determine that at least one electrode of the pair of electrodes is losing electrical contact with the skin of the subject in response to detecting that the changes in the at least one transthoracic impedance parameter exceeds the corresponding baseline level by the threshold, and
to issue an alert in response to a determination that the at least one electrode of the pair of electrodes is losing electrical contact with the skin of the subject.

2. The life support device of claim 1, further comprising:
a user interface including at least one of an audio output device and a video output device; and
at least one processor, electrically coupled to the therapy interface, the transthoracic impedance monitor, and user interface, the at least one processor being configured to present a message on the at least one of the audio output device and the video output device in response to receiving the alert.

3. The life support device of claim 2, wherein the message indicates that the at least one electrode of the pair of electrodes is losing electrical contact with the skin of the subject.

4. The life support device of claim 3, wherein the transthoracic impedance monitor is configured to identify the frequency of the CPR chest compressions based on a fundamental frequency of the transthoracic impedance signal.

5. The life support device of claim 1, wherein the transthoracic impedance monitor is further configured to detect CPR chest compressions based on a signal indicative of the CPR chest compressions.

6. The life support device of claim 5, wherein the transthoracic impedance monitor is configured to receive the signal indicative of the frequency of the CPR chest compressions from one of a compression sensor and a mechanical chest compression device and to identify the frequency of the CPR chest compressions based on the signal.

7. The life support device of claim 6, wherein the transthoracic impedance monitor is further configured to correlate at least one of the slope of the high frequency waveform component of the transthoracic impedance signal and the shape of the high frequency waveform component of the transthoracic impedance signal with the frequency of the CPR chest compressions.

8. The life support device of claim 7, further comprising a filter electrically coupled to the therapy interface, the filter being configured to filter out frequencies of the high frequency waveform component of the transthoracic impedance signal that do not correspond to the frequency of the CPR chest compressions and harmonics thereof.

9. The life support device of claim 8, wherein the transthoracic impedance parameters further include an amount of background noise at frequencies other than a frequency of the high frequency waveform component and harmonics of the high frequency waveform component.

10. The life support device of claim 9, wherein the transthoracic impedance parameters further include an amplitude of the transthoracic impedance signal.

11. A method of detecting a loss of electrical contact between at least one electrode of a pair of electrodes that are electrically coupled to a skin of a subject, comprising acts of:
monitoring transthoracic impedance parameters of a transthoracic impedance signal between the pair of electrodes, wherein the transthoracic impedance signal has a high frequency waveform component that varies with a frequency of CPR chest compressions, and wherein the transthoracic impedance parameters include at least one of a slope of the high frequency waveform component of the transthoracic impedance signal, a shape of the high frequency waveform component of the transthoracic impedance signal, and a relative energy content of the high frequency waveform component of the transthoracic impedance signal at a fundamental frequency of the transthoracic impedance signal and/or at a harmonic of the fundamental frequency of the transthoracic impedance signal;
establishing baseline levels of the transthoracic impedance parameters;
detecting whether changes in at least one transthoracic impedance parameter exceeds the a corresponding baseline level by a threshold;
determining, prior to loss of electrical contact between the at least one electrode of the pair of electrodes and the skin of the subject, that the at least one electrode of the pair of electrodes is losing electrical contact with the skin of the subject in response to the at least one transthoracic impedance parameter exceeding the corresponding baseline level by the threshold; and
issuing an alert in response to a determination that the at least one electrode of the pair of electrodes is losing electrical contact with the skin of the subject.

12. The method of claim 11, further comprising detecting an occurrence of CPR chest compressions based upon a signal indicative of the CPR chest compressions.

13. The method of claim 12, wherein the act of detecting an occurrence of CPR chest compressions includes one of analyzing the transthoracic impedance signal to identify the frequency of the CPR chest compressions based on a fundamental frequency of the transthoracic impedance signal and receiving the signal indicative of the CPR chest compressions from one of a compression sensor and a mechanical chest compression device and identifying the frequency of the CPR chest compressions based on the signal.

14. The method of claim 13, further comprising an act of correlating at least one of the slope of the high frequency waveform component of the transthoracic impedance signal and the shape of the waveform of the transthoracic impedance signal with the frequency of the CPR chest compressions.

15. The method of claim 14, further comprising an act of filtering frequencies of the high frequency waveform component of the transthoracic impedance signal that do not correspond to the frequency of the CPR chest compressions and harmonics thereof.

16. The method of claim 15, wherein the act of monitoring transthoracic impedance parameters further includes monitoring an amount of background noise at frequencies other than a frequency of the high frequency waveform component and harmonics of the high frequency component.

17. The method claim 12, further comprising acts of:
determining whether the signal indicative of the CPR compressions is from one of a compression sensor and a mechanical chest compression device; and
adjusting the threshold in response to a determination that the signal is from one of the compression sensor and the mechanical chest compression device.

18. A life support device, comprising:
a pair of electrodes configured to be attached to a skin of a subject;
a therapy interface electrically coupled to the pair of electrodes; and
a transthoracic impedance monitor electrically coupled to the therapy interface, the transthoracic impedance monitor being configured to
monitor transthoracic impedance parameters of a transthoracic impedance signal between the pair of electrodes, wherein the transthoracic impedance signal has a high frequency waveform component that varies with a frequency of CPR chest compressions, and wherein the transthoracic impedance parameters include at least one of a slope of the high frequency waveform component of the transthoracic impedance signal, a shape of the high frequency waveform component of the transthoracic impedance signal, and a relative energy content of the high frequency waveform component of the transthoracic impedance signal at a fundamental frequency of the transthoracic impedance signal and/or at a harmonic of the fundamental frequency of the transthoracic impedance signal,
to establish baseline levels of the transthoracic impedance parameters,
to detect whether changes in at least one transthoracic impedance parameter exceeds a corresponding baseline level by a threshold,
to determine that at least one electrode of the pair of electrodes is losing electrical contact with the skin of the subject in response to detecting that the changes in the at least one transthoracic impedance parameter exceeds the corresponding baseline level by the threshold, and
to issue an alert in response to a determination that the at least one electrode of the pair of electrodes is losing electrical contact with the skin of the subject.

* * * * *